(12) United States Patent
Isaacs

(10) Patent No.: US 7,056,886 B2
(45) Date of Patent: Jun. 6, 2006

(54) GLP-2 FORMULATIONS

(75) Inventor: Indu J. Isaacs, Andover, MA (US)

(73) Assignee: NPS Allelix, Corp., Mississauga (CA)

( * ) Notice: Subject to any disclaimer, the term of this patent is extended or adjusted under 35 U.S.C. 154(b) by 628 days.

(21) Appl. No.: 09/750,022

(22) Filed: Dec. 29, 2000

(65) Prior Publication Data

US 2001/0027180 A1 Oct. 4, 2001

(30) Foreign Application Priority Data

Dec. 30, 1999 (GB) .............................. 9930882

(51) Int. Cl.
- A61K 38/00 (2006.01)
- A61K 38/26 (2006.01)
- C07K 14/00 (2006.01)

(52) U.S. Cl. ......................... 514/12; 530/308; 530/399; 530/324; 435/4; 435/287.1

(58) Field of Classification Search ................ 514/12; 530/308, 399, 324; 435/4, 287.1
See application file for complete search history.

(56) References Cited

U.S. PATENT DOCUMENTS 4,985,244 A * 1/1991 Makino et al. ............... 424/89
5,652,216 A * 7/1997 Kornfelt et al. ............. 514/12
5,912,229 A * 6/1999 Thim et al. .................. 514/12
5,952,301 A * 9/1999 Drucker ....................... 514/12
5,997,856 A * 12/1999 Hora et al. ................. 424/85.2
6,120,761 A * 9/2000 Yamazaki et al. .......... 424/85.1

FOREIGN PATENT DOCUMENTS

WO 97/39031 10/1997
WO 98/03547 1/1998
WO 99/43361 9/1999

OTHER PUBLICATIONS

Buhl et al., Naturally Occurring Products of Proglucagon 111–160 in the Porcine and Human Samll Intestine, J. Biol. Chem. 263, 8621–8624 (1988).*

Lund et al., Anglerfish Islet Pre–proglucagon II, Nucleotide and corresponding amino acid Sequenmce of the cDNA, J. Biol. Chem. 258, 3280–3284 (1983).*

* cited by examiner

Primary Examiner—Jon Weber
Assistant Examiner—Chih-Min Kam
(74) Attorney, Agent, or Firm—Foley & Lardner LLP

(57) ABSTRACT

The invention is directed to formulations of GLP-2 peptides and analogs thereof exhibiting superior stability following storage and/or exposure to elevated temperatures. The GLP-2 compositions comprise a GLP-2 peptide or an analog thereof, a phosphate buffer, L-histidine, and mannitol.

75 Claims, 6 Drawing Sheets

Figure 1. Amino acids screening in buffers using heat stress.
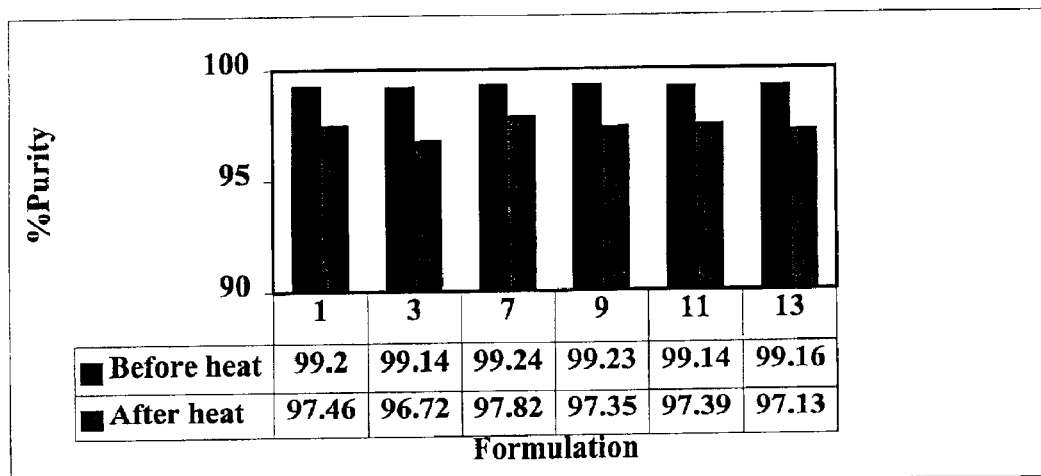
Formulation
1. 10 mM Phosphate, 10 mM Glu
3. 10 mM Phosphate, 10 mM Citrate
7. 10 mM Phosphate, 10 mM Ser
9. 10 mM Phosphate, 10 mM Pro
11. 10 mM Phosphate, 10 mM His
13. 10 mM Phosphate, 10 mM Gly Figure 2. Screening of buffers using heat stress.
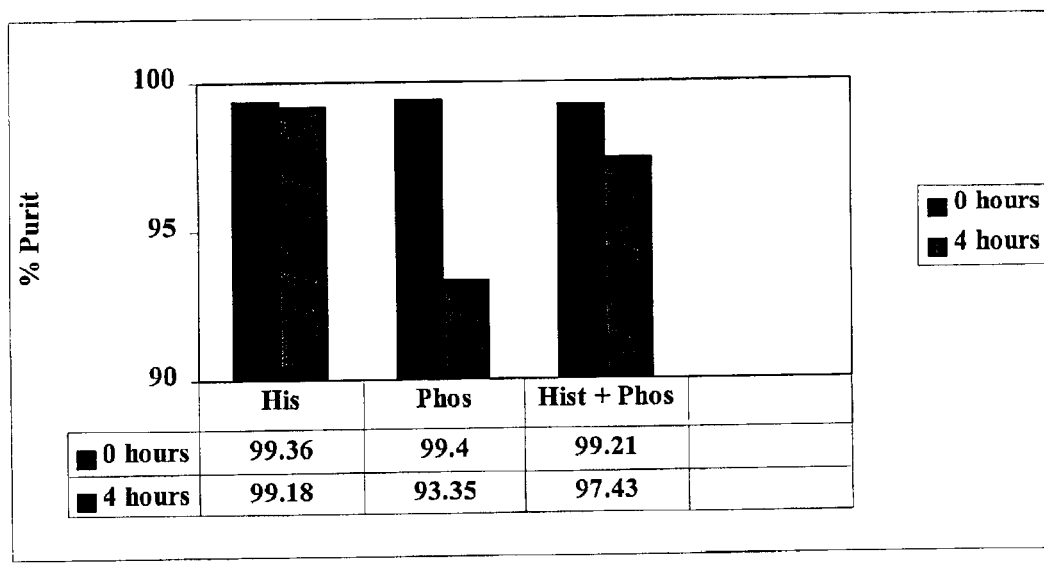

Figure 3. Screening of Bulking agents analyzed by RP-HPLC.
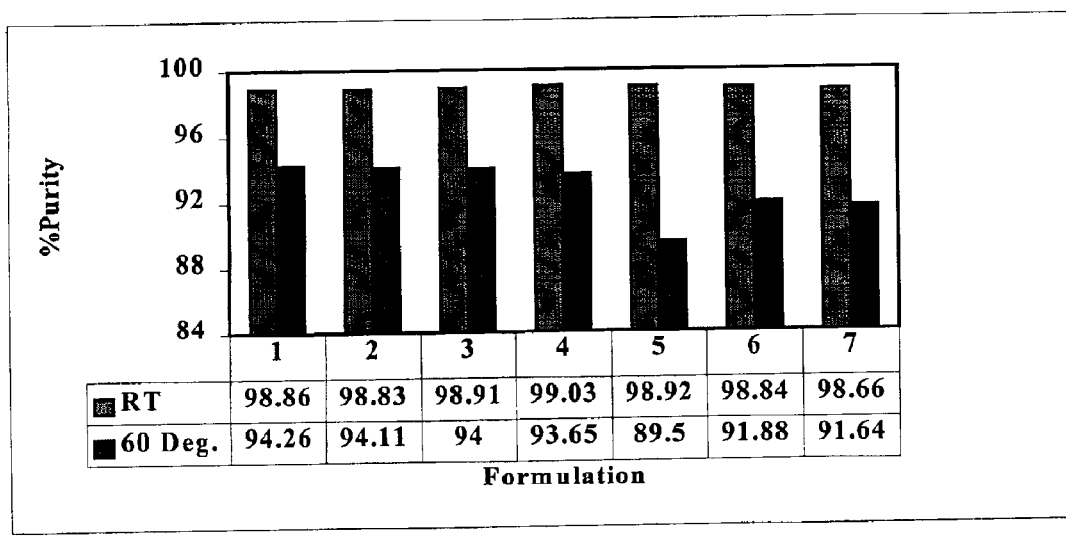
Formulation
1. 25 mM Histidine, 35 mM phosphate, 3% Mannitol
2. 50 mM Histidine, 35 mM phosphate, 3% Mannitol
3. 75 mM Histidine, 35 mM phosphate, 3% Mannitol
4. 25 mM Histidine, 25 mM phosphate, 3% sucrose
5. 25 mM Histidine, 25 mM phosphate, 3% trehalose
6. 25 mM Histidine, 25 mM phosphate, 3% maltose
7. 25 mM Histidine, 25 mM phosphate, 3% lactose Figure 4. Bulking agents analyzed by SE-HPLC.
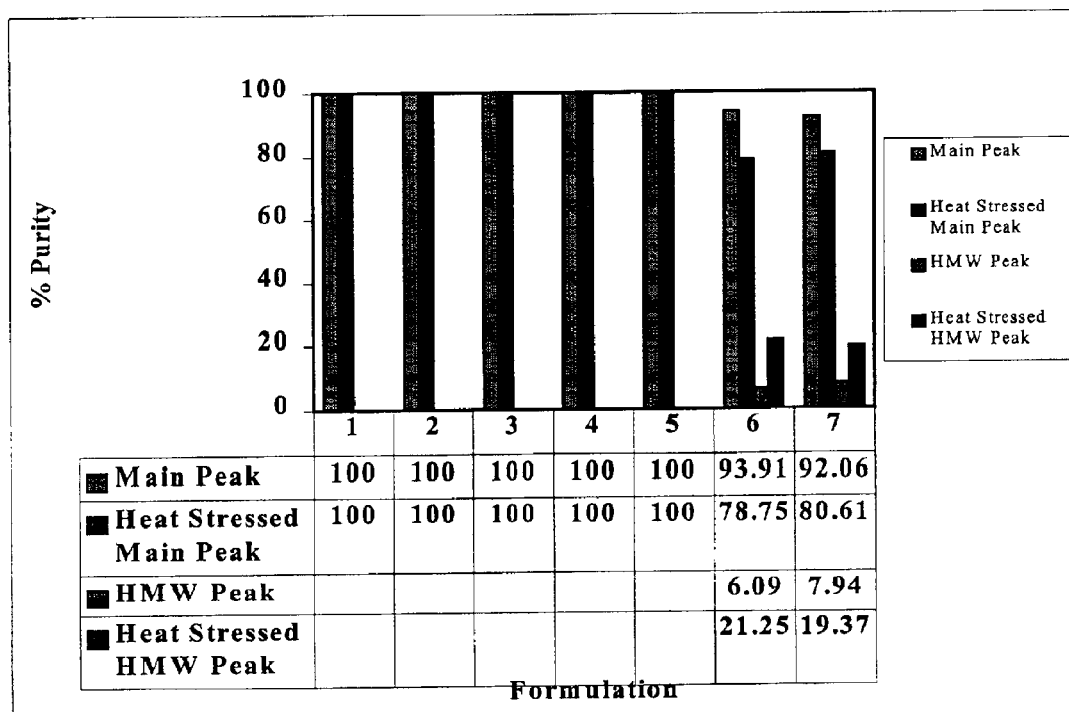
Formulation
1. 25 mM Histidine, 35 mM phosphate, 3% Mannitol
2. 50 mM Histidine, 35 mM phosphate, 3% Mannitol
3. 75 mM Histidine, 35 mM phosphate, 3% Mannitol
4. 25 mM Histidine, 25 mM phosphate, 3% sucrose
5. 25 mM Histidine, 25 mM phosphate, 3% trehalose
6. 25 mM Histidine, 25 mM phosphate, 3% maltose
7. 25 mM Histidine, 25 mM phosphate, 3% lactose Figure 5. Stability of liquid formulations stored at 4 °C.
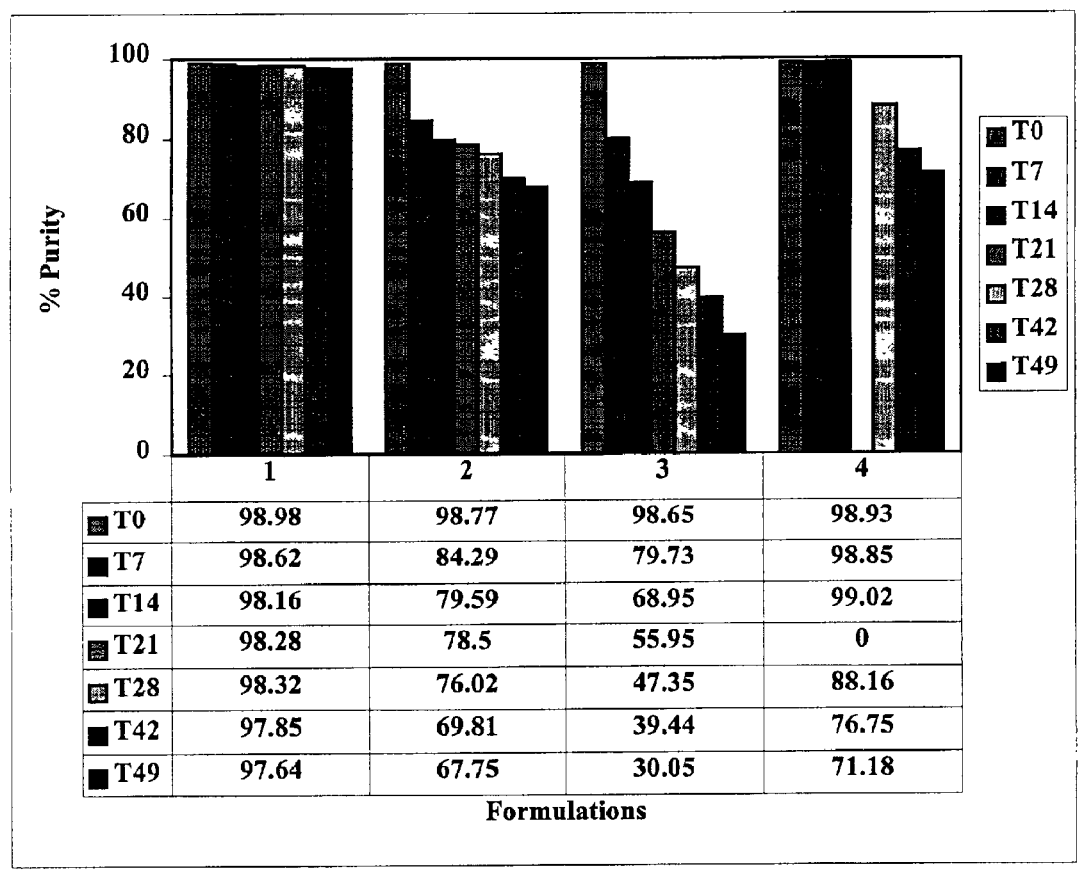
| | 1 | 2 | 3 | 4 |
|---|---|---|---|---|
| T0 | 98.98 | 98.77 | 98.65 | 98.93 |
| T7 | 98.62 | 84.29 | 79.73 | 98.85 |
| T14 | 98.16 | 79.59 | 68.95 | 99.02 |
| T21 | 98.28 | 78.5 | 55.95 | 0 |
| T28 | 98.32 | 76.02 | 47.35 | 88.16 |
| T42 | 97.85 | 69.81 | 39.44 | 76.75 |
| T49 | 97.64 | 67.75 | 30.05 | 71.18 |
Formulations
1. 35 mM Phosphate, 50 mM Histidine, 3% Mannitol, pH 7.4
2. 35 mM Phosphate, 50 mM Histidine, 5% Sucrose, pH 7.4
3. 35 mM Phosphate, 25 mM Lysine, 3% Mannitol, pH 7.4
4. 35 mM Phosphate, 25 mM Lysine, 5% Mannitol, pH 7.4

Figure 6. Heat stressed samples.
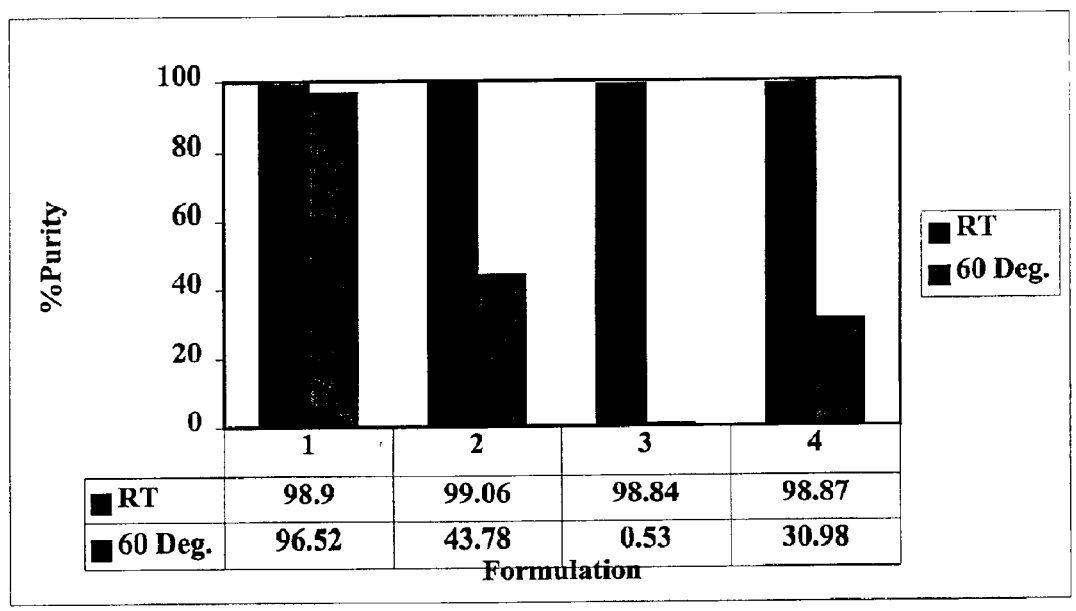
Formulations
1. 35 mM Phosphate, 50 mM Histidine, 3% Mannitol, pH 7.4
2. 35 mM Phosphate, 50 mM Histidine, 5% Sucrose, pH 7.4
3. 35 mM Phosphate, 25 mM Lysine, 3% Mannitol, pH 7.4
4. 35 mM Phosphate, 25 mM Lysine, 5% Mannitol, pH 7.4

GLP-2 FORMULATIONS

FIELD OF INVENTION

The present invention provides formulations for GLP-2 peptides and analogs thereof. In particular, the invention provides formulations of GLP-2 peptides and GLP-2 analogs with improved stability.

BACKGROUND OF THE INVENTION

Administration of therapeutic peptides requires peptide formulations that remain stable during storage. In general, parenteral administration is used with peptides because of their increased size and subsequent difficulty in crossing biological membranes. Peptides can be particularly difficult to formulate because of their tendency to degrade over time and/or undergo aggregation and precipitation. Degradation, aggregation, and precipitation are all indicative of an unstable formulation. Such an unstable formulation is not commercially viable, as it cannot pass U.S. Food and Drug Administration approval.

Formulation variables which affect the degradation of peptides during storage include, but are not limited to, pH, the quantity of salts present, and the type and quantity of excipients. In addition, temperatures, pressures, and time for freezing and drying cycles can affect the stability of a lyophilized peptide formulation. The role of most of these variables has been studied; however, the synergistic effect of the variables is still poorly understood.

Glucagon-like peptide-2 (GLP-2) is a 33 amino acid peptide having therapeutic applications in the treatment of diseases of the gastrointestinal tract. In particular, it has been determined that GLP-2 and analogs thereof act as trophic agents to enhance and maintain the functioning of the gastrointestinal tract and to promote growth of intestinal tissue. See e.g., U.S. Pat. Nos. 5,834,428; 5,789,379; and 5,990,077; and International Publication No. WO 98/52600.

Commercial exploitation of GLP-2 or an analog thereof requires a stable GLP-2 formulation that can be readily prepared using a commercially acceptable process. Because GLP-2 is a protein, and thus far more labile than traditional small molecular weight drugs, the formulation of GLP-2 or an analog thereof presents challenges not commonly encountered by the pharmaceutical industry. For example, methionine oxidation at position 10 and aspargine deamination at position 11, 16, and/or 24 of GLP-2 are potential routes of degradation. Furthermore, GLP-2 or an analog thereof may also be adsorbed to surfaces to form aggregates and/or precipitate, which would then render the formulation unstable.

There is a need in the art for stable formulations of GLP-2 peptides and analogs thereof which can be prepared using a commercially acceptable process. The present invention satisfies these needs.

SUMMARY OF THE INVENTION

The present invention provides stable formulations of GLP-2 and analogs thereof, which can be prepared using a commercially acceptable process.

It has been discovered that relatively high concentrations of GLP-2 can be used in pharmaceutically acceptable formulations. Moreover, it has been discovered that a pH of greater than about 5.5, more preferably greater than about 6, even more preferably from about 6.9 to about 7.9, and most preferably about 7.3 to about 7.4, is suitable for a stable formulation.

It has also been discovered that the GLP-2 analog h[Gly2] GLP-2 undergoes a phase transition between 40–55° C., depending upon the salt concentration, and becomes hydrophobic in the presence of salt. It has also been discovered that Tween 80®, salt, and arginine are not suitable materials for producing a stable formulation for h[Gly2]GLP-2.

According to one aspect of the present invention, there is provided a GLP-2 formulation comprising: (1) a medically useful amount of GLP-2; (2) a phosphate buffer sufficient to adjust the pH of the formulation to a pharmaceutically acceptable level, and in particular above about 6.0; (3) a stabilizing amount of the amino acid L-histidine; and (4) a bulking agent selected from sucrose and mannitol.

More particularly, there is provided a GLP-2 formulation comprising: (1) a medically useful amount of GLP-2 comprising from about 0.1 to about 50 mg/ml of GLP-2, preferably about 5 to about 40 mg/ml, more preferably about 7 to about 30 mg/ml, even more preferably about 10 to about 20 mg/ml, and most preferably about 20 mg/ml; (2) a phosphate buffer to maintain the pH at a physiologically tolerable level, i.e., above 6; (3) a stabilizing amino acid, particularly L-Histidine; and (4) a bulking agent, particularly mannitol. All percentages described herein (except for percentages for water) are weight/volume of formulated product prior to lyophilization in gms/ml (×100). Percentages for water content are weight/weight of lyophilized product (×100).

In one embodiment of the present invention, the GLP-2 formulation is a h[Gly2]GLP-2 lyophilized formulation comprising in the reconstituted product: (1) phosphate buffer in an amount necessary to maintain the pH of the reconstituted product between about 6.9–7.9, and preferably in an amount to maintain a pH of about 7.3 to about 7.4; (2) about 0.5 to about 1% L-histidine; (3) about 2 to about 5% mannitol, preferably about 2.5 to about 3.5% mannitol, and most preferably about 3% mannitol; and (4) from about 0.1 to about 50 mg/ml of GLP-2 or an analog thereof, preferably about 5 to about 40 mg/ml, more preferably about 7 to about 30 mg/ml, even more preferably about 10 to about 20 mg/ml, and most preferably about 20 mg/ml.

In a more preferred embodiment of the invention, a h[Gly2]GLP-2 lyophilized formulation is provided comprising in the reconstituted product: (1) about 7 to about 30 mg/ml, preferably about 10 to about 20 mg/ml, and most preferably about 20 mg/ml of h[Gly2]GLP-2; (2) a phosphate buffer sufficient to maintain the pH at about 7.3 to about 7.4; (3) about 0.5 to about 1% L-histidine; and (4) about 3% mannitol.

In another aspect of the present invention there is provided a process for making the lyophilized formulation of GLP-2. Such a process comprises the following steps:

(a) preparing the GLP-2 formulation comprising GLP-2 or an analog thereof, a phosphate buffer, L-histidine, and mannitol;

(b) freezing the formulation to about −40° C.;

(c) performing a first drying step at about −20° C.; and (d) performing a second drying step at +20° C.

In a preferred embodiment the liquid formulation subjected to the lyophilization process comprises:

(1) the h[Gly2]GLP-2 analog; (2) 35 mM phosphate buffer to maintain the reconstituted product at a pH of about 6.9 to about 7.9, and more preferably at a pH of about 7.3 to about 7.4; (3) about 0.5 to about 1% L-histidine; and (4) about 3% mannitol.

According to another aspect of the present invention, there is provided a method for preparing a GLP-2 pharmaceutically acceptable formulation for parenteral administration, comprising the step of reconstituting the lyophilized GLP-2 formulation.

There is further provided in accordance with the present invention a therapeutically useful kit comprising: (1) a sterile vial comprising a lyophilized GLP-2 formulation of the invention, (2) a vehicle suitable for reconstitution thereof, preferably sterile water, (3) instructions for reconstitution; and (4) optionally instructions for administration. The kit may further comprise a device suitable for injection of the reconstituted preparation.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1: Shows a bar graph of the effect of certain amino acid stabilizers on a formulation of h[Gly2]GLP-2 using a heat stress test. The precent (%) purity is plotted for three different amino acid formulations, both before and after the application of heat;

FIG. 2: Shows a bar graph of the effect of L-histidine on a phosphate buffered formulation of h[Gly2]GLP-2. The % purity is plotted for three different formulations at 0 and at 4 hours;

FIG. 3: Shows a bar graph of the screening of bulking agents analyzed by reverse-phase high performance liquid chromatography (RP-HPLC) at room temperature and 60° C. The % purity is plotted for seven different amino acid formulations;

FIG. 4: Shows a bar graph of the screening of bulking agents analyzed by size exclusion high performance liquid chromatography (SE-HPLC). "HMW" represents a high molecular weight peak. The % purity is plotted for seven different formulations;

FIG. 5: Shows a bar graph of the stability of mannitol and sucrose formulations of h[Gly2]GLP-2 in a liquid state, prior to lyophilization, which have been stored at 4° C. The % purity is plotted for four different formulations at 0 min. through 49 min., at 7 min. intervals; and FIG. 6: Shows a bar graph of the stability of lyophilized mannitol and sucrose formulations of h[Gly2]GLP-2 which have been stored at 60° C. The % purity is plotted for four different amino acid formulations.

DETAILED DESCRIPTION OF THE INVENTION

The invention relates to GLP-2 formulations which exhibit superior storage stability. The term "GLP-2," as used herein, means a naturally occurring GLP-2 peptide or a GLP-2 analog thereof (unless specifically indicated otherwise).

The present GLP-2 formulations can be provided as liquid formulations suitable for administration, such as by injection, in unit or multi-dose amounts. The liquid formulations can also serve as stock solution from which lyophilized dosage forms can be prepared. Accordingly, the present GLP-2 formulations can also be provided in lyophilized form, e.g., as freeze-dried powders suitable for reconstitution and subsequent administration as injectable liquid formulations.

Lyophilized formulations of the present invention exhibit storage stability of six months at ambient temperature, and eighteen months at 4° C. Storage stability is exhibited by minimal peptide degradation, preferably less than about 5% peptide degradation, more preferably less than about 3 to about 4% peptide degradation, and even more preferably less than about 1 to about 2% peptide degradation. Peptide degradation can be measured using standard reverse-phase HPLC (RP-HPLC) techniques.

The naturally occurring GLP-2 peptides are highly conserved peptides. Accordingly, GLP-2 peptides for use in the present invention include the various naturally produced forms of GLP-2, particularly vertebrate species (including piscine and avian species), more particularly mammalian (such as primate, rodent (including rat, mouse, degu, hamster, and guinea pig), porcine, and bovine,), and more particularly the human form. Desirably, but not essentially, the naturally occurring GLP-2 peptide selected for use is of the same species as the subject identified for treatment.

GLP-2 analogs potentially useful in the present invention include agonists and antagonists of the GLP-2 receptor. GLP-2 agonists activate the GLP-2 receptor by first binding to the receptor, followed by stimulating an intracellular second messenger system coupled to the receptor. In one embodiment of the invention, the GLP-2 agonists act selectively at the GLP-2 receptor. Selectively-acting GLP-2 agonists are compounds that, in the context of a suitable GLP-2 receptor binding or functional assay, bind to the GLP-2 receptor with greater affinity. Such greater affinity is preferably at least an order of magnitude greater relative to different receptor types, such as the GLP-1 receptor. In other embodiments, the GLP-2 analogs bind to the GLP-2 receptor with an affinity at least equivalent to the affinity of naturally occurring GLP-2.

In other embodiments of the invention, the GLP-2 peptide is an analog of natural GLP-2 that incorporates one or more amino acid substitutions, additions, deletions, or modifications and retains biological acitivity.

The agonist activity of human GLP-2 and rat GLP-2 is believed to require an intact N-terminus, but various deletions of up to several residues at the C-terminus are tolerated without loss of agonist activity. Substitutions are tolerated at sites outside regions conserved across the various GLP-2 species homologs. Similarly, substitutions are also tolerated at sites within regions conserved across GLP-2 species. In preferred embodiments, the amino acid substitutions are conservative substitutions. For example, one member of an amino acid class can be substituted by another member, e.g., the substitution of alanine by glycine, the substitution of asparagine by glutamine, the substitution of methionine by leucine or isoleucine, and the like.

Antagonist activity of GLP-2 analogs in humans and rats is exhibited when the naturally occurring GLP-2 peptide is mutated in any one or more of the first four N-terminal residues, in particular by deleting any one or more of these N-terminal residues. In addition, antagonist activity is exhibited when naturally occurring hGLP-2 is substituted: (1) with an amino acid which does not naturally occur at any of the following positions: $Asp^{15}$, $Phe^{22}$, $Thr^{29}$, $Thr^{32}$ and/or $Asp^{33}$; (2) and when $Ala^2$ is replaced by anyone of the following amino acids: Leu, Cys, Glu, Arg, Trp and $PO_3$-$Tyr^2$. In addition, antagonists of GLP-2 analogs include any mutation or variation of the naturally occurring GLP-2 peptide which results in the inhibition of intestinotrophic activity of naturally occurring GLP-2 or GLP-2 analogs which exhibit agonist acitivity. Structural analogs of GLP-2 which act as antagonists are specifically described in WO 98/03547.

The GLP-2 receptor analogs can be identified by screening peptides against cells genetically engineered to produce the GLP-2 receptor. The GLP-2 receptor has been cloned. See Munroe et. al., *Proc. Natl. Acad. Sci. USA*, 96(4):1569 (1999). Cells functionally incorporating the GLP-2 receptor, and their use to screen GLP-2 analogs, are also described in International Publication No. WO 98/25955, published on Jun. 18, 1998.

In a preferred embodiment, the GLP-2 analog with agonist activity has been altered to confer resistance to degradation by endogenous enzymes, such as DPP-IV. Such analogs suitably incorporate a replacement of the alanine residue at position 2. In specific embodiments, the Ala2 residue is replaced by glycine or serine, or by other residues as described for example in U.S. Pat. No. 5,789,379. In a preferred embodiment, the GLP-2 receptor agonist is [Gly2] GLP-2. For use in treating humans, the GLP-2 analog is desirably but not essentially a human GLP-2 peptide or analog, particularly including the Gly2 analog of human GLP-2.

It was discovered that the h[Gly2]GLP-2 analog precipitated at a pH of less than 5.5, and that temperature profiles suggested a heat-induced and salt-dependent transition temperature of about 40° C. Based on pH solubility profiles, it was determined that a phosphate buffer provides optimal buffering capacity for GLP-2 peptides. Furthermore, the addition of L-histidine to the phosphate buffer was found to effectively stabilize GLP-2 peptides, whereas the addition of arginine citrate or lysine did not effectively stabilize GLP-2 compositions. L-histidine acts as a stabilizing amino acid that increases the length of time that the GLP-2 peptide remains intact prior to degradation.

The lyophilized formulations of the present invention are preferably provided in a powder form comprising not more than about 5% water by weight, preferably not more than 2% water by weight, and more preferably not more than about 1% water by weight.

The bulking agent incorporated in the preparation produces a non-crystalline amorphous cake. It was found that lactose, trehalose, and maltose sugars did not effectively stabilize the GLP-2 formulation as well as mannitol and sucrose. Mannitol was found to be the preferred excipient for the GLP-2 formulations.

The buffering agent incorporated in the formulation of the present invention is selected from those capable of buffering the preparation to a pH within a physiologically tolerable range for administration to a patient. "Physiologically tolerable" formulations are those that elicit reactions, in a recipient, that are not so extreme as to preclude further administration of the formulation. acceptable range for administration to a patient. More particularly, it was found that the pH of the formulation should by greater than about 5.5, more preferably greater than about 6, even more preferably of about 6.9 to about 7.9, and most preferably about 7.3 to about 7.4. Preferably, the buffering agent is phosphate based, and most preferably a 35 mM phosphate buffer is used.

The formulations of the present invention incorporate GLP-2 in a medically effective amount, namely an amount which is useful either therapeutically or diagnostically. Such an amount can be determined based on the type of GLP-2 peptide or analog selected and on the intended end-use of the preparation. Therapeutically useful amounts of GLP-2 include those unit dosage amounts useful in a regimen to treat a subject that would benefit from GLP-2 administration, as described more fully in U.S. Pat. Nos. 5,834,428; 5,789,379; 5,990,077; and 5,952,301, and in International Publication No. WO 98/52600.

In one application, the formulation maybe exploited for the treatment of gastrointestinal disease, particularly diseases, disorders or conditions of the intestine. Therapeutically useful amounts also include multi-dose amounts of GLP-2, which can be delivered to an intended subject. Diagnostically useful amounts of GLP-2 include those amounts useful as a calibrant when assessing endogenous levels of GLP-2 or levels of GLP-2 drug in a subject, for instance as a prelude to GLP-2 therapy, or during the course of GLP-2 treatment. Medically useful amounts of GLP-2 thus can range widely from a few micrograms to many milligrams. The formulations of the present invention preferably provide about 0.1 to about 50 mg/ml of GLP-2, preferably about 5 to about 40 mg/ml, more preferably about 7 to about 30 mg/ml, even more preferably about 10 to about 20 mg/ml, and most preferably about 20 mg/ml of GLP-2.

In an embodiment of the invention, a liquid formulation of h[Gly2]GLP-2 suitable for lyophilization comprises: (1) preferably about 7 to about 30 mg/ml, even more preferably about 10 to about 20 mg/ml, and most preferably about 20 mg/ml of h[Gly2]GLP-2; (2) about 2 to about 5% of mannitol, preferably about 2.5 to about 3.5%, most preferably about 3%; (3) about 0.5 to about 1% of an amino acid stabilizer, which is preferably L-histidine; and (4) a phosphate buffer in an amount capable of buffering the reconstituted product to a pH of about 6.9–7.9, and preferably a pH of about 7.3 to about 7.4.

The GLP-2 formulations of the present invention are preferably filled in individual vials to the desired volume and the vials are subjected to a lyophilization process. The lyophilization process includes a temperature cycling process that is carefully controlled to ensure that drying proceeds uniformly. The drying process is continued until there is less than about 5% of water, preferably less than about 2% of water, and more preferably no more than about 1% of water, in the GLP-2 formulation.

A lyophilization process suitable for the present invention involves a freezing step and a two-step drying process. In an exemplary freezing process: (1) the formulation vials are first cooled from ambient temperature to about −1° C. at about 2 C/minute, and then held at about −1° C. for about 15 minutes, (2) next the vials are cooled from about −1° C. to about −40° C. at about 2° C./minute, and then held at about −40° C. for about 4 hours.

In an exemplary first drying cycle, the temperature is increased from about −40° C. to about −20° C. at about 2° C./minute, and then held at about −20° C. for about 14 hours under a vacuum of about 150 mT with a condenser temperature of about −80° C. In an exemplary second drying cycle, the vials are warmed from about −20° C. to about +20° C. at about 2° C./minute, and then held at about +20° C. for about 14 hours at a vacuum of about 150 mT and a condenser temperature of about −80° C. until there is less than about 5% of water, preferably less than about 2% of water, and more preferably no more than about 1% of water. The vials are then preferably stored at about 4° C.

The present invention also provides a medically useful kit comprising: (1) at least one vial containing the lyophilized freeze-dried GLP-2 formulation of the invention; (2) at least one vial of sterile water for reconstitution; (3) instructions directing reconstitution; and (4) optionally an injection device for administration. To use the kit, the user mixes the water with the formulation vial, preferably by transferring the water to the formulation vial. The lyophilized formulation of the present invention rapidly dissolves upon reconstitution and, when reconstituted, is stable for at least about 12 hours, preferably up to about 24 hours, at 4° C. In a preferred embodiment, reconstitution of the lyophilized formulation is carried out using sterile water, preferably no more than about 1 mL of sterile water per dose of GLP-2. To reconstitute, the sterile water may be drawn into a syringe and then transferred to the vial containing the lyophilized GLP-2 formulation.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

Formulation and Lyophilization of h[Gly2]GLP-2

The purpose of this example was to prepare a lyophilized formulation of the GLP-2 peptide h[Gly2]GLP-2.

A base formulation buffer, comprising 35 mM sodium phosphate at pH 7.4, was prepared as follows: (1) purified water was added to a sterile, depyrogenated flask; (2) sodium heptahydrate was added to the flask; and (3) monobasic sodium phosphate monohydrate was added to the flask. The buffer was mixed and the pH was verified to be 7.4±0.2. The base formulation buffer was then used to dilute the GLP-2 peptide h[Gly2]GLP-2 liquid bulk drug substance to a concentration of 10 mg/ml. L-histidine was then added to a final concentration of 7.76 gm/L, and mannitol was added to a final concentration of 30 gm/L.

The preparation was carefully mixed, followed by filtering the preparation through a 0.22 μm filter into a sterile filling tank. The GLP-2 preparation was then aseptically filled, in 1 ml aliquots, from the tank into 3 cc sterile USP Type I glass vials, which were then partially capped with sterile rubber stoppers and placed into lyophilization trays.

The vials were then loaded into the lyophilizer, and the lyophilization cycle was commenced by pre-freezing the formulation to a temperature of −40±2° C. for about 4 hours. In the freezing step, the formulation vials were first cooled from ambient temperature to −1° C. at 2° C./minute and then held at −1° C. for approximately 15 minutes. This first freezing step was followed by cooling the vials from −1° C. to −40° C. at 2° C./minute, and the vials were then maintained at −40° C. for 4 hours.

In the first and primary drying cycle, the temperature was increased from −40° C. to −20° C. at 2° C./minute and then held at −20° C. for about 14 hours under a vacuum of 150 mT with a condenser temperature of −80° C. In the second drying cycle, the vials were warmed from −20° C. to +20° C. at 2° C./minute and then held at +20° C. for about 14 hours at a vacuum of 150 mT and a condenser temperature of −80° C. The second drying cycle was continued until there is less than about 5% of water, preferably less than about 2% of water, and more preferably no more than about 1% of water, remaining in the GLP-2 formulation. The vials were then stored at 4° C.

At the end of the lyophilization cycle, the vials were purged with filtered nitrogen and the rubber stoppers were fully depressed into the vials. The stoppered vials were removed from the lyophilizer and permanently sealed with a crimped aluminum seal and capped with a polypropylene flip-off button.

EXAMPLE 2

Screening of Amino Acid to Stabilize the Formulation

The purpose of this example was to determine the effect of various amino acid additives on the stability of GLP-2 following exposure to elevated temperatures.

The h[Gly2]GLP-2 formulation was tested with several amino acids as set out below. The tested formulations comprised: (1) h[Gly2]GLP-2 at a concentration of 10 mg/ml; and (2) the additives listed below. The pH of the composition was maintained between 7.1–7.5.

1. 10 mM phosphate, 10 mM Glutamate
2. 10 mM phosphate, 10 mM Glutamate, 50 mM Arginine
3. 10 mM phosphate, 10 mM Citrate
4. 10 mM phosphate, 10 mM Citrate, 50 mM Arginine
5. 10 mM phosphate, 100 mM Citrate
6. 10 mM phosphate, 100 mM Citrate, 50 mM Arginine
7. 10 mM phosphate, 10 mM Serine
8. 10 mM phosphate, 10 mM Serine, 50 mM Arginine
9. 10 mM phosphate, 10 mM Proline
10. 10 mM phosphate, 10 mM Proline, 50 mM Arginine
11. 10 mM phosphate, 10 mM Histidine
12. 10 mM phosphate, 10 mM Histidine, 50 mM Arginine
13. 10 mM phosphate, 10 mM Glycine
14. 10 mM phosphate, 10 mM Glycine, 50 mM Arginine
15. 10 mM His, 10 mM Glycine
16. 10 mM His, 10 mM Glycine, 50 mM Arginine Following preparation, the samples were lyophilized according to the protocol of Example 1, stored at 40° C. for 14 days, diluted to 0.4 mg/ml, and then heated at 60° C. for 4 hours.

All of the formulations containing arginine precipitated upon heating (Formulations 2, 4, 6, 8, 10, 12, 14, and 16). Formulation 5 (100 mM citrate) and Formulation 15 (L-histidine and glycine) also precipitated. Formulations comprising L-histidine, 10 mM citrate, serine, proline, glutamate, and glycine (Formulations 1, 3, 7, 9, 11, and 13) showed similar stability when these compounds were used without the addition of other amino acids. (See FIG. 1.)

As shown in FIG. 2, when L-histidine was used as a stabilizer in combination with a phosphate buffer, the GLP-2 peptide remained stable following heat stress for 4 hours at 60° C.

EXAMPLE 3

Screening Bulk Agents

The purpose of this example was to determine the effect of various bulk agent additives on the stability of a GLP-2 peptide following exposure to elevated temperatures.

The following formulations of the GLP-2 peptide h[Gly2]GLP-2, at a concentration of 0.4 mg/ml, were lyophilized according to lyophilization process of Example 1. The compositions were then reconstituted and heated to 60° C.

1. 25 mM histidine, 35 mM phosphate, 3% mannitol
2. 50 mM histidine, 35 mM phosphate, 3% mannitol
3. 75 mM histidine, 35 mM phosphate, 3% mannitol
4. 25 mM histidine, 25 mM phosphate, 3% sucrose
5. 25 mM histidine, 25 mM phosphate, 3% trehalose
6. 25 mM histidine, 25 mM phosphate, 3% maltose 7. 25 mM histidine, 25 mM phosphate, 3% lactose As shown in FIGS. 3 and 4, the reverse phase HPLC data (FIG. 3) demonstrate that the mannitol samples (Formulations 1, 2, and 3) exhibited the least amount of GLP-2 degradation. In addition, all three L-histidine concentrations (25 mM, 50 mM, and 75 mM) showed comparable stability. The SE-HPLC analysis (FIG. 4) also showed that, except for maltose and lactose (Formulations 6 and 7), the GLP-2 analog in all of the formulations eluted as a single peak without aggregation. Formulations 6 and 7 gave an additional high molecular weight (HMW) impurity peak that accounted for approximately 6%. However when these samples were heat stressed at 60° C, the high molecular weight impurity aggregates increased to approximately 20% in Formulations 6 and 7.

Accordingly, mannitol and sucrose were determined to be acceptable candidates for addition to the GLP-2 formulations of the invention.

EXAMPLE 4

Screening Bulk Agents

The purpose of this example was to compare the effectiveness of the bulk agent additives sucrose and mannitol on the stability of GLP-2 following exposure to elevated temperatures.

The following formulations of h[Gly2]GLP-2, at 10 mg/ml, were prepared and the stability of GLP-2 in each formulation was analyzed. The concentration of sucrose in Formnulation 2 was increased to 5% to satisfy physiological osmolarity.

1. 35 mM phosphate, 50 mM histidine, 3% mannitol, pH 7.4

2. 35 mM phosphate, 50 mM histidine, 5% sucrose, pH 7.4

3. 35 mM phosphate, 25 mM lysine, 3% mannitol, pH 7.4

4. 35 mM phosphate, 25 mM lysine, 5% mannitol, pH 7.4

The formulations were then lyophilized according to lyophilization process of Example 1, followed by reconstitution, and stability testing. The formulations were then heated to 60° C. for 4 hours, followed by stability testing.

All of the lyophilized samples stored at room temperature and at 40° C. remained stable.

The stability of the formulations following lyophilization and exposure to elevated temperatures was then measured. Formulation 1, comprising L-histidine and mannitol, did not show evidence of GLP-2 degradation. However, Formulations 2, 3, and 4, comprising histidine/sucrose, lysine/mannitol, and lysine/mannitol, respectively, showed evidence of GLP-2 degradation over time (see FIG. 6).

These results suggest that the addition of sucrose and lysine destabilizes the GLP-2 peptide (see also FIG. 5), following exposure to elevated temperatures.

EXAMPLE 5

The Purity and Quantity of h[Gly2]GLP-2

The purity of the GLP-2 is a measurement of peptide degradation or lack thereof. The quantity of GLP-2 is a measurement of the total content of the GLP-2 and hence it is an indication as to the quantative amounts of peptide degradation, precipatation and/or aggregation.

To determine the purity and quantity of h[Gly2]GLP-2 reverse-phase HPLC is employed. Reverse phase chromatography is a bonded phase chromatographic technique that allows separation of compounds on the basis of their polarity. h[Gly2]GLP-2 is adsorbed onto the hydrophobic silica-based bonded reverse phase packing material of the column and is eluted as a single peak by increasing the hydrophobicity of the mobile phase with an acetonitrile gradient. The h[Gly2]GLP-2 sample is quantitated against a reference standard.

Equipment
Waters HPLC system or equivalent
Vydac (Hesperia, Calif.), C18 reverse-phase analytical column, 4.6 mm×25 cm, 5 μm particle size, 300 Å pore size, or equivalent
Vydac (Hesperia, Calif.), C18 analytical guard cartridge, 4.6×30 mm, 5 μm particle size, 300 Åpore size, or equivalent
Hamilton Digital Syringe or equivalent
Pipettes
Materials
Membrane filters (0.45 μm)
HPLC standard glass vials, polypropylene inserts, and PTFE septa
Acetonitrile, HPLC grade
Milli-Q water
Trifluoroacetic acid (TFA), spectro grade
Ammonium bicarbonate, ACS grade
1M ammonium hydroxide
Procedure

| Chromatograhic conditions: | |
|---|---|
| Mobile phase: | Eluent A: 0.1% (v/v) TFA in Milli-Q water |
|  | Eluent B: 0.1% (v/v) TFA in acetonitrile |
| Autosampler: | 2–8° C. |
| Detector: | wavelength set at 214 nm and sensitivity at 2 AU |
| Run time: | 45 minutes |

| Gradient conditions: | | | |
|---|---|---|---|
| Time (minutes) | Flow Rate (mL/min) | % Eluent B | Curve Shape |
| 0 | 1.0 | 30 | 6 |
| 1 | 1.0 | 30 | 6 |
| 30 | 1.0 | 60 | 6 |
| 35 | 1.0 | 30 | 6 |
| 45 | 1.0 | 30 | 6 |

Store column in 20% acetonitrile after use.

Preparation of 10 mM Ammonium Bicarbonate, pH 8 Buffer:

Dissolve 0.20 gram of ammonium bicarbonate in approximately 200 mL of Milli-Q water. Adjust the pH to 8.0±0.1 using 1 M ammonium hydroxide. Add Milli-Q water to final volume of 250 mL. Set expiration date of one week and store at 2–8° C. Allow buffer to warm to room temperature, then check pH and filter buffer through 0.45 μm filter prior to use.
Preparation of Standard:

Reconstitute h[Gly2]GLP-2 reference standard with filtered 10 mM ammonium bicarbonate, pH 8 buffer, to a concentration of 200 μg/mL.
Preparation of Sample:

Reconstitute/dilute h[Gly2]GLP-2 test sample(s) in the same buffer used for the standard, to a concentration of 200 μg/mL. Prepare duplicate samples.
Analysis:

Inject 50 μL of standard solution 6 times, the % RSD of h[Gly2]GLP-2 peak retention time and area is not more than (NMT) 5%, the USP tailing factor of the h[Gly2]GLP-2 peak is between 1–2.

Inject 50 μL of blank (filtered 10 mM ammonium bicarbonate, pH 8 buffer) once.

Inject 50 μL of h[Gly2]GLP-2 test sample once.

Inject 50 μL of standard solution once after ten injections of test sample and at the end of the run.

Data Processing and Calculations

Data Processing

Set the software provided with the HPLC system to integrate the area under every peak observed between 5 and 40 minutes, not including any peaks that correspond to those observed in the chromatogram of the blank injection.

Calculations $$\% \text{ Purity} = \frac{h[Gly2]GLP-2 \text{ peak area} \times 100}{\text{area of all peaks detected}}$$

$$\text{Concentration} = \frac{(h[Gly2]GLP-2 \text{ peak area of sample} \times \text{conc. of standard}) \times \text{Dilution Factor }(DF)}{\text{ave. }h[Gly2]GLP-2 \text{ peak area of standard}}$$

EXAMPLE 6

A lyophilized formulation of 9 mg/ml of h[Gly2]GLP-2 was prepared in accordance with the method of example 1. This sample was tested for stability by measuring the purity and drug content of the sample at 4° C. and 25° C. using the method of Example 4. The results are presented in Table 1 and Table 2. As shown in the tables, the sample exhibited stability for at least 6 months and 18 months at 4° C. and 25° C., respectively.

TABLE 1

Storage Condition: 4° C.

| TEST METHOD | Time 0 | 3 Months | 6 Months | 9 Months | 12 Months | 18 Months |
|---|---|---|---|---|---|---|
| pH | 7.4 | 7.4 | 7.2 | 7.0 | 7.4 | 7.4 |
| Purity by RP-HPLC | 99.3% | 99.5% | 99.3% | 99.1% | 99.0% | 99.4% |
| Content by RP-HPLC (mg/ml) | 9.0 | 8.7 | 8.9 | 8.7 | 8.7 | 8.8 |
| Water Content or Residual Moisture (w/w) | 1.0% | 1.0% | 1.0% | 1.0% | 1.0% | 1.2% |

TABLE 2

Storage Condition: 25° C.

| TEST METHOD | Time 0 (release) | 1 Month | 2 Months | 3 Months | 4 Months | 5 Months | 6 Months |
|---|---|---|---|---|---|---|---|
| pH | 7.4 | 7.4 | 7.5 | 7.4 | 7.2 | 7.3 | 7.2 |
| Purity by RP-HPLC | 99.3% | 99.5% | 99.3% | 99.6% | 99.3% | 99.3% | 99.4% |
| Content by RP-HPLC | 9.0 | 8.7 | 9.1 | 8.8 | 9.3 | 8.7 | 9.0 |
| Water Content or Residual Moisture (w/w) | 1.0% | 1.2% | 1.2% | 1.2% | 1.3% | 2.0% | 1.3% |

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

I claim:

1. A glucagon-like peptide 2 (GLP-2) formulation comprising:
    (a) a medically useful amount of a naturally occurring GLP-2 or an analog thereof;
    (b) a phosphate buffer in an amount sufficient to adjust the pH of the formulation to a physiologically tolerable level;
    (c) L-histidine; and
    (d) a bulking agent selected from the group consisting of mannitol and sucrose.

2. The GLP-2 formulation of claim 1, wherein the pH of the formulation is greater than about 6.0.

3. The GLP-2 formulation of claim 2, wherein the GLP-2 peptide is h(Gly2)GLP-2.

4. The GLP-2 formulation according of claim 2, wherein the pH of the formulation is from about 6.9 to about 7.9.

5. The GLP-2 formulation of claim 4, wherein the GLP-2 peptide is h(Gly2)GLP-2.

6. The GLP-2 formulation of claim 4, wherein the pH of the formulation is from about 7.3 to about 7.4.

7. The GLP-2 formulation of claim 6, wherein the GLP-2 peptide is h(Gly2)GLP-2.

8. The GLP-2 formulation of claim 1, wherein the GLP-2 peptide or analog thereof is present at a concentration of about 0.1 to about 50 mg/ml.

9. The GLP-2 formulation of claim 8, wherein the GLP-2 peptide is h(Gly2)GLP-2.

10. The GLP-2 formulation of claim 8, wherein the GLP-2 peptide or analog thereof is present at a concentration of about 5 to about 40 mg/ml.

11. The GLP-2 formulation of claim 10, wherein the GLP-2 peptide is h(Gly2)GLP-2.

12. The GLP-2 formulation of claim 10, wherein the GLP-2 peptide or analog thereof is present at a concentration of about 7 to about 30 mg/ml.

13. The (GLP-2 formulation of claim 12, wherein the GLP-2 peptide is h(Gly2)GLP-2.

14. The GLP-2 formulation of claim 12, wherein the GLP-2 peptide or analog thereof is present at a concentration of about 10 to about 20 mg/ml.

15. The GLP-2 formulation of claim 14, wherein the GLP-2 peptide is h(Gly2)GLP-2.

16. The GLP-2 formulation of claim 14, wherein the L-histidine is present in an amount of about 0.5 to about 1%.

17. The GLP-2 formulation of claim 16, wherein the GLP-2 peptide is h(Gly2)GLP-2.

18. The GLP-2 formulation of claim 16, wherein the bulking agent is mannitol.

19. The GLP-2 formulation of claim 18, wherein the GLP-2 peptide is h(Gly2)GLP-2.

20. The GLP-2 formulation of claim 18, wherein the mannitol is present at a concentration of about 2 to about 5%.

21. The GLP-2 formulation of claim 20, wherein the GLP-2 peptide is h(Gly2)GLP-2.

22. The GLP-2 formulation of claim 20, wherein the mannitol is present at a concentration of about 2.5 to about 3.5%.

23. The GLP-2 formulation of claim 22, wherein the GLP-2 peptide is h(Gly2)GLP-2.

24. The GLP-2 formulation of claim 1, wherein the GLP-2 peptide is selected from the group consisting of a mammalian GLP-2 peptide, a vertebrate GLP-2 peptide, and a human GLP-2 peptide.

25. The GLP-2 formulation of claim 24, wherein the GLP-2 peptide is h(Gly2)GLP-2.

26. The GLP-2 formulation of claim 24, wherein the GLP-2 peptide has the sequence of a GLP-2 species from an animal selected from the group consisting of a primate, rat, mouse, porcine species, oxine species, bovine species, degu, hamster, guinea pig, fish, chicken, and human.

27. The GLP-2 formulation of claim 26, wherein the GLP-2 peptide is h(Gly2)GLP-2.

28. The GLP-2 formulation of claim 27, which is stable at ambient temperature for up to 6 months, as evidenced by GLP-2 peptide degradation of less than about 5% during this time period.

29. The GLP-2 formulation of claim 28, wherein less than about 4% peptide degradation is observed after storage of the GLP-2 formulation during the time period.

30. The GLP-2 formulation of claim 29, wherein less than about 2% peptide degradation is observed after storage of the GLP-2 formulation during the time period.

31. The GLP-2 formulation of claim 1, wherein the GLP-2 analog is identified by a process comprising:
 (a) screening peptides against cells genetically engineered to produce the GLP-2 receptor, and
 (b) identifying peptides which bind to the GLP-2 receptor, wherein such peptides are identified as GLP-2 peptides useful in the formulation of claim 1.

32. The GLP-2 formulation of claim 1, wherein the GLP-2 peptide is an analog of natural GLP-2, the analog having:
 (a) one or more amino acid substitutions, additions, deletions, or modifications; and
 (b) GLP-2 receptor binding activity.

33. The GLP-2 formulation of claim 1, wherein the GLP-2 peptide is an analog which has been altered to confer resistance to endogenous enzymes.

34. The GLP-2 formulation of claim 33, wherein the alteration comprises substitution of the alanine residue at position 2 of GLP-2 with another suitable amino acid.

35. The GLP-2 formulation of claim 34, wherein the alanine residue at position 2 is substituted with glycine or serine.

36. The GLP-2 formulation of claim 1, wherein the GLP-2 analog is a GLP-2 receptor antagonist.

37. The GLP-2 formulation of claim 36, wherein the GLP-2 receptor antagonist has either (1) an amino acid substitution selected from the group consisting of $Asp^{15}$, $Phe^{22}$, $Thr^{29}$, $Thr^{32}$, $Asp^{33}$, and combinations thereof; or (2) an amino acid substitution of Ala at position 2 by an amino acid selected from the group consisting of Leu, Cys, Glu, Arg, Trp and $PO_3$—-Tyr, wherein the residue or position for the amino acid substitution is numbered according to a mammalian GLP-2.

38. The GLP-2 formulation of claim 1 in lyophilized form.

39. The lyophilized formulations of claim 38, comprising less than about 5% water by weight.

40. The lyophilized formulations of claim 39, comprising 2% or less water by weight.

41. The GLP-2 formulation of claim 1, which is stable at a temperature of about 4° C. for up to 18 months, as evidenced by GLP-2 peptide degradation of less than about 5% during this time period.

42. The GLP-2 formulation of claim 41, wherein less than about 4% peptide degradation is observed after storage of the GLP-2 during the time period.

43. The GLP-2 formulation of claim 42, wherein less than about 2% peptide degradation is observed after storage of the GLP-2 formulation during the time period.

44. The GLP-2 formulation of claim 1, wherein said GLP-2 analog has one or more amino acid substitutions, additions, deletions, or modifications and has GLP-2 receptor binding activity.

45. The GLP-2 formulation of claim 1, wherein the GLP-2 peptide is h(Gly2)GLP-2.

46. A GLP-2 formulation comprising:
 (a) about 0.1 to about 50 mg/ml of a GLP-2 peptide or an analog thereof;
 (b) a phosphate buffer in an amount sufficient to adjust the pH of the formulation to a pharmaceutically tolerable level;
 (c) about 0.5 to about 1% L-histidine; and
 (d) about 2 to about 5% mannitol.

47. The GLP-2 formulation of claim 46, wherein the GLP-2 is h(Gly2)GLP-2.

48. The GLP-2 formulation of claim 47, wherein the formulation is lyophilized.

49. The GLP-2 formulation of claim 47, wherein the pH of the formulation is selected from the group consisting of greater then about 6.0, and from about 6.9 to about 7.9.

50. The GLP-2 formulation of claim 49, wherein the pH of the formulation is from about 7.3 to about 7.4.

51. The GLP-2 formulation of claim 46, wherein said GLP-2 analog has one or more amino acid substitutions, additions, deletions, or modifications and has GLP-2 receptor binding activity.

52. A GLP-2 formulation comprising:
 (a) a medically useful amount of a naturally occurring GLP-2 peptide or an analog thereof;
 (b) a phosphate buffer in an amount sufficient to adjust the pH of the formulation to a physiologically tolerable level;
 (c) L-histidine in an amount sufficient to stabilize the formulation; and
 (d) a bulking agent selected from the group consisting of mannitol and sucrose.

53. A method for making a lyophilized formulation of GLP-2 comprising the following steps:
 (a) preparing a GLP-2 formulation comprising:
  (i) a GLP-2 peptide or an analog thereof;
  (ii) a phosphate buffer in an amount sufficient to adjust the pH of the formulation to a pharmaceutically tolerable level;

(iii) L-histidine; and
(iv) a hulking agent selected from the group consisting of mannitol and sucrose;
(b) freezing the formulation to −40° C.;
(c) drying the formulation in a first drying step at −20° C; and
(d) drying the formulation in a second drying step at +20° C.

54. The method of claim 53, wherein the pH of the GLP-2 formulation prior to freezing is selected from the group consisting of greater than about 6.0, and from about 6.9 to about 7.9.

55. The method of claim 54, wherein the pH of the formulation is from about 7.3 to about 7.4.

56. The method of claim 53, wherein the freezing process of step (b) comprises:
(a) cooling the formulation from ambient temperature to about −1° C. at about 2° C./minute, followed by maintaining the formulation at about −1° C. for about 15 minutes; and
(b) cooling the formulation from about −1° C. to about −40° C. at about 2° C./minute, followed by maintaining the formulation at about −40° C. for about 4 hours.

57. The method of claim 53, wherein the drying process of step (c) comprises:
(a) raising the temperature from about −40° C. to about −20° C. at about 2° C./minute; and
(b) maintaining the formulation at about −20° C. for about 14 hours under a vacuum of about 150 mT with a condenser temperature of about −80° C.

58. The method of claim 53, wherein the drying process of step (d) comprises:
(a) warming the formulation from about −20° C. to about +20° C. at about 2° C./minute;
(b) maintaining the formulation at about +20° C. for about 14 hours at a vacuum of about 150 mT and a condenser temperature of about −80° C. until there is less than about 5% of water remaining in the formulation.

59. The method of claim 58, wherein the formulation is maintained at about +20° C., at a vacuum of about 150 mT and a condenser temperature of about −80° C., until there is about 2% or less of water remaining in the formulation.

60. The method of claim 53, wherein said GLP-2 analog has one or more amino acid substitutions, additions, deletions, or modifications and has GLP-2 receptor binding activity.

61. A kit comprising:
(a) a lyophilized GLP-2 formulation comprising:
(i) a GLP-2 peptide or an analog thereof;
(ii) a phosphate buffer in an amount sufficient to adjust the pH of the formulation to a pharmaceutically acceptable level;
(iii) L-histidine; and
(iv) a bulking agent selected from the group consisting of mannitol and sucrose;
(b) a vial of sterile water for reconstitution; and
(c) instructions directing reconstitution.

62. The kit of claim 61, wherein the pH of the GLP-2 formulation is selected from the group consisting of greater than about 5.5, greater than about 6.0, and from about 6.9 to about 7.9.

63. The kit of claim 62, wherein the pH of the formulation is from about 7.3 to about 7.4.

64. The kit of claim 63, wherein the GLP-2 peptide is h(Gly2)GLP-2.

65. A kit of claim 61, further comprising an injection device for administration.

66. The kit of claim 61, wherein following reconstitution the GLP-2 formulation is stable for at least about 12 hours.

67. The kit of claim 61, wherein following reconstitution the GLP-2 formulation is stable for up to about 24 hours.

68. The kit of claim 61, wherein said GLP-2 analog has one or more amino acid substitutions, additions, deletions, or modifications, and has GLP-2 receptor binding activity.

69. A method for treating a human or animal having a gastrointestinal disorder, disease or condition for which treatment with GLP-2 is indicated, the method comprising the step of administering a therapeutically effective amount of a GLP-2 formulation comprising:
(a) a GLP-2 peptide or an analog thereof;
(b) a phosphate buffer in an amount sufficient to adjust the pH of the formulation to a pharmaceutically tolerable level;
(c) L-histidine; and
(d) a bulking agent selected from the group consisting of mannitol and sucrose,
thereby enhancing, maintaining, or promoting the growth or functioning of the gastrointestinal tract.

70. The method of claim 69, wherein the pH of the GLP-2 formulation is selected from the group consisting of greater than about 5.5, greater than about 6.0, and from about 6.9 to about 7.9.

71. The method of claim 70, wherein the pH of the formulation is from about 7.3 to about 7.4.

72. The method of claim 70, wherein the GLP-2 peptide is h(Gly2)GLP-2.

73. The method of claim 69, wherein the GLP-2 formulation is administered by injection.

74. The method of claim 69, wherein the GLP-2 formulation is administered by infusion.

75. The method of claim 69, wherein said GLP-2 analog has one or more amino acid substitutions, additions, deletions, or modifications and has GLP-2 receptor binding activity.

* * * * *